United States Patent [19]

Arpe

[11] 4,093,666
[45] June 6, 1978

[54] PROCESS FOR THE MANUFACTURE OF GLYCOL ETHER FORMALS

[75] Inventor: Hans-Jürgen Arpe, Fischbach, Taunus, Germany

[73] Assignee: Hoechst Aktiengesellschaft, Frankfurt (Main), Germany

[21] Appl. No.: 741,392

[22] Filed: Nov. 12, 1976

Related U.S. Application Data

[63] Continuation of Ser. No. 546,901, Feb. 4, 1975, abandoned.

[30] Foreign Application Priority Data

Feb. 6, 1974 Germany .............................. 2405633

[51] Int. Cl.$^2$ ............................................. C07C 41/00
[52] U.S. Cl. ................................................. 260/615 A
[58] Field of Search ..................................... 260/615 A

[56] References Cited

U.S. PATENT DOCUMENTS

| | | | |
|---|---|---|---|
| 2,331,367 | 10/1943 | Baggett | 260/615 A |
| 2,785,949 | 3/1957 | Kress | 260/615 A |
| 2,796,401 | 6/1957 | Matuszak et al. | 260/615 A |
| 2,796,423 | 6/1957 | Cottle et al. | 260/615 A X |
| 2,800,513 | 7/1957 | Hall et al. | 260/615 A |
| 3,329,614 | 7/1967 | Milnes et al. | 260/615 A |
| 3,435,077 | 3/1969 | Henckel et al. | 260/615 A X |

FOREIGN PATENT DOCUMENTS

| | | | |
|---|---|---|---|
| 1,293,143 | 4/1969 | Germany | 260/615 A |
| 2,163,907 | 1/1972 | Germany | 260/615 A |

*Primary Examiner*—Howard T. Mars
*Attorney, Agent, or Firm*—Curtis, Morris & Safford

[57] ABSTRACT

Ethylene glycol monomethyl ether formals of the formula $[CH_3O(CH_2CH_2O)_n/_2CH_2$ in which n is in the range of from 1 to 8, are obtained by reacting at least one ethylene glycol monoethyl ether with a 20 to 60% by weight aqueous formaldehyde solution in the presence of an aliphatic chloro- or chloro-fluoro-hydrocarbon having a boiling point of from 35° to 125° C at atmospheric pressure and in the presence of, as a catalyst, a strong acid having a pK value of less than 4, and distilling off the water in the form of an azeotropic mixture.

10 Claims, No Drawings

PROCESS FOR THE MANUFACTURE OF GLYCOL ETHER FORMALS

This is a continuation of application Ser. No. 546,901 filed Feb. 4, 1975 now abandoned.

This invention relates to a process for the manufacture of formals, i.e. acetals of formaldehyde, of the formula $[CH_3O(CH_2CH_2O)_n]_2CH_2$ by reacting ethylene glycol monomethyl ethers, or more simply "glycol monoethers", of the general formula $CH_3O(CH_2CH_2O)_nH$ in which $n$ is in the range of from 1 to 8 with aqueous formaldehyde solutions in the presence of acid catalysts.

It is known to react alcohols and in particular glycol monoethers having a primary alcohol function with paraformaldehyde or more advantageously with trioxane (cf. German Pat. No. 1,293,143) to obtain formals. The two substances yielding formaldehyde are prepared from aqueous formaldehyde solutions, as obtained in the industrial manufacture of formaldehyde by oxidation of methanol, by at least one further process step. Hence, paraformaldehyde and trioxane are less economic starting materials for making formals than an aqueous formaldehyde solution.

However, the literature indicates various disadvantages for the manufacture of formals from alcohols and aqueous formaldehyde solutions. According to H. Meerwein in Houben-Weyl, Methoden der Org. Chemie, 4th edition, Stuttgart 1965, volume VI/3, page 210, attempts to remove water by azeotropic distillation resulted in an incomplete separation or no separation at all because of the distillation of a water-alcohol-aldehyde mixture. To dehydrate the distillate drying agents have been proposed, for example calcium carbide, anhydrous cupric sulfate or calcium chloride. This method is complicated and considerable amounts of salt solutions are obtained from which products which have distilled over, such as formaldehyde and alcohols, must be separated and recycled into the reaction with the catalyst.

An attempt to react ethylene glycol monomethyl ether with aqueous formaldehyde solution in the presence of an acid catalyst confirmed the aforesaid fact, i.e. the distillate consisted of a water-glycol monoether-formaldehyde mixture. The use of benzene, toluene, or heptane as water entrainer changed little in the quantitative composition of the distillate.

In the manufacture of formals generally strong acids are used as catalysts, for example $H_2SO_4$, HCl, p-toluene-sulfonic acid and the like, as well as Lewis acids such as $FeCl_3$. Acid ion exchangers have also been proposed (cf. U.S. Pat. No. 2,566,599). With their use and with a 4 to 5 molar excess of, for example, butanol, a yield of 64 mole % of butanol formal, calculated on paraformaldehyde, can be obtained.

According to German Pat. No. 1,293,143 trioxane can be reacted, in the presence of an acid ion exchanger, with a 6 to 9 fold excess of an alcohol, calculated on the trioxane, i.e. a 2 to 3 fold excess of the formaldehyde content of the trioxane, with a selectivity of approximately 90 mole %, calculated on the alcohol.

Hence, it follows that, in spite of the use of very different acid catalysts, satisfactory selectivities can only be obtained when an excess of alcohol is used, so that large amounts of alcohol must be recycled. This fact and the high price of the compound used to produce the formaldehyde, i.e. paraformaldehyde or trioxane, decrease the economy of the above manufacturing processes.

It is an object of the present invention to provide a process for the manufacture of ethylene glycol monomethyl ether formal of the formula $[CH_3O(CH_2CH_2O)_n]_2CH_2$, in which $n$ is in the range of from 1 to 8, by reacting the corresponding ethylene glycol monoethyl ethers with formaldehyde in the presence of an acid catalyst, which comprises reacting one or several ethylene glycol monomethyl ethers with an aqueous formaldehyde solution of 20 to 60% strength by weight in the presence of an aliphatic chloro- or chloro-fluoro-hydrocarbon boiling at a temperature of from 35° to 125° C at atmospheric pressure and in the presence of 0.2 to 20% by weight, calculated on the glycol monoether(s), of a strong acid having a pK value below 4 as catalyst, and distilling off the water in the form of an azeotropic mixture.

The advantages of the claimed process reside in the fact that the most economic substance yielding formaldehyde can be used, i.e. an aqueous formaldehyde solution, and that the disadvantages of distilled over reaction components are avoided. Above all, the process of the invention gives high yields of formals even with the use of stoichiometric amounts of the reaction components.

A further surprising advantage is obtained by the use of the chloro- or chloro-fluoro-hydrocarbons as auxiliaries. It is known that ethylene glycol monomethyl ether $CH_3OCH_2CH_2OH$ forms an azeotropic mixture with water (15.3% by weight in admixture with water) on the composition of which commonly used entrainers, such as benzene, toluene, or aliphatic hydrocarbons, for example heptane, have hardly any influence.

As reported in Houben-Weyl, Methoden der Org. Chemie, volume I/1, Stuttgart 1958, page 867 there are neither substances which are suitable separating aids for all binary azeotropes nor is there a method by which such a substance can be determined a priori for a given mixture.

It is, therefore, surprising that the chloro- and chloro-fluoro-hydrocarbons, in addition to their known property as entrainers, do have a separating effect on the three component system formaldehyde-glycol monoether-water. That is to say, with their use the aqueous distillate is practically free from glycol monoether.

Suitable chloro- and chloro-fluoro-hydrocarbons are all those the boiling point of which at atmospheric pressure is in the range of from 35° to 125° C, such as di-, tri-, or tetrachloromethane, ethylene dichloride, 1,1,2-trichloroethane, 1,1,2-trichlorotrifluoroethane, tetrachloroethylene, isopropyl chloride, propyl chloride, propylene dichloride and butyl chloride. Especially preferred are di-, tri- and tetrachloromethane since each has a low boiling point and forms an azeotrope which also has a low boiling point, a sufficient water content in the azeotrope and is readily available on an industrial scale.

The relatively low boiling chloro- and chloro-fluoro-hydrocarbons, which can be used in the process of the invention, have the advantage that only a small proportion of formaldehyde escapes from the reaction mixture by distilling out of the equilibrium with its hydrate form.

Suitable glycol monoethers of the above formula to be used for the reaction are the monomethyl ethers of mono-, di-, tri-, tetra-, penta-, hexa-, hepta-, and octaethylene glycol. These monoethers can be readily obtained on an industrial scale by a catalyzed reaction of methanol with a corresponding or different amount of ethylene oxide. They can be used either in the form of a uniform substance or in the form of mixtures.

The formals obtained by the process of the invention can be used, for example, as stabilizers for acrylonitrile polymers or as solvents for making cellulose ester or ether lacquers. They are also suitable starting materials for the preparation of dimethyl ethers of the glycols.

In the process in accordance with the invention the proportion by weight of the chloro- or chloro-fluoro-hydrocarbons, used as entrainer and separating aid, to the glycol monoether(s) can vary within wide limits, for example in the range of from 0.2 : 1 to 5 : 1, preferably 0.5 : 1 to 3 : 1. In general, the formaldehyde and the glycol monoether are used in stoichiometric proportions, i.e. 1 mole of formaldehyde for 2 moles of glycol monoether. When, for the further use of the glycol monoether formal the quantitative absence of either formaldehyde or glycol monoether is required, the glycol or the aldehyde components should be used in a slight excess, for example from 10 to 20 mole %, so that owing to the very selective and complete reaction a distillation of the glycol monoether formals which, in the case of higher formals with $n$ greater than 3 would cause losses by thermal decomposition, can be dispensed with.

Suitable strong acids having a pK value below 4 are mineral acids or aliphatic or aromatic sulfonic acids, such as sulfuric acid, hydrochloric acid, phosphoric acid, p-toluene-sulfonic acid, or naphthalene-sulfonic acid. Because of the easy handling of a heterogeneous acid catalyst and owing to the fact that cation exchangers do not have a corrosive effect, strongly acid cross-linked sulfonic acid group-containing polystyrenes are particularly suitable as catalysts. They are generally used in the form of spheres having a diameter of from 0.2 to 2 mm. Suitable strongly acid commercial ion exchangers are, for example Amberlyst ® 15 (Rohm & Haas, Philadelphia, USA) or Lewatit ® S 100 (Bayer, Germany). Further suitable strongly acid ion exchangers are listed by K. Dorfner in "Ionenaustauscher", Berlin 1964, pages 15 - 31.

The amount of the strongly acid ion exchanger to be used, calculated on the glycolmonoether(s), ranges from 0.2 to 20 and preferably 0.5 to 10% by weight.

Depending on the mixing ratio, the reaction temperature in the reaction mixture of glycol monoether, aqueous formaldehyde and chloro- or chloro-fluoro-hydrocarbon is normally in the range of from 40° to 125° C and such that the halohydrocarbon or its azeotrope with water refluxes. The reaction temperature should be preferably below 100° C to keep as low as possible the loss of formaldehyde by distillation out of the reaction mixture. This can be reached, for example, by increasing the proportion by weight of the halohydrocarbon to the glycol monoether, for example, from 0.5 : 1 to 3 : 1.

To carry out the reaction the components glycol monoether and aqueous formaldehyde solution are usually heated in a commonly used reaction vessel, for example a flask or vessel with stirrer, to boiling temperature together with the halohydrocarbon and the acid catalyst. The water from the formaldehyde solution and the reaction water are separated, with the aid of a water separator, in the form of an azeotropic mixture with the halohydrocarbon. The halohydrocarbon is recycled into the reaction vessel. It has proved advantageous to install, between the reaction vessel and the water separator, a rectifying column in order to reduce the formaldehyde content in the azeotrope.

Another advantageous mode of carrying out the reaction consists in refluxing the glycol monoether together with the catalyst and a halohydrocarbon and introducing the aqueous formaldehyde solution continuously in dosed quantities. A low formaldehyde partial pressure in the reaction vessel results in a smaller discharge of formaldehyde in the aqueous distillate.

The parameters for conversion, selectivity and yield used in the following examples are defined as follows:

The conversion of the components used, that is to say glycol monoether(s) and formaldehyde is the percentage in moles of reacted component calculated on used component.

The selectivity of a formal is its molar amount in percent, calculated on one reacted component.

The yield of a formal is its molar amount in percent, calculated on the quantity of one of the components used.

The following examples illustrate the invention.

EXAMPLE 1

760 g (10 moles) of ethylene glycol monomethyl ether, 500 ml of chloroform and 100 g of an acid ion exchanger (Amberlyst ® 15) were heated while stirring in a 2 liter three-necked flask provided with stirrer, dropping funnel and a water separator for use of an entrainer having a density greater than 1. The proportion by weight of chloroform to glycol monoether was 0.98 : 1. During the course of 3 hours 405 g of a 37% aqueous formaldehyde solution, corresponding to 150 g or 5 moles of formaldehyde, were uniformly introduced in measured quantities. While stirring and refluxing the water of the formaldehyde solution and the reaction water were distilled as an azeotrope into the water separator over a column having about 2 or 3 theoretical plates, and separated. The aqueous distillate contained 10.4 g. (0.34 mole) of formaldehyde and no glycol monoether. The reaction product contained 4.28 moles of formal of the glycol monoether and 0.93 mole of unreacted glycol monoether.

The conversion of the glycol monoether was 90.7 mole %, the conversion of the formaldehyde amounted to 93.2 mole %. The yield of glycol monoether formal was 85.5 mole %, corresponding to selectivities of 94.5 mole %, calculated on the glycol monoether and 97.4 mole %, calculated on the formaldehyde.

EXAMPLE 2

The reaction was carried out under the conditions specified in Example 1, but the amount of chloroform was reduced so that its proportion by weight to the glycol monoether amounted to 0.59 : 1. In this reaction the formaldehyde content in the distillate rose to 0.61 mole. The conversion of glycol monoether dropped to 87 mole %.

EXAMPLE 3

The reaction was carried out as specified in Example 1 with the exception that the chloroform was replaced by 500 ml of carbon tetrachloride (proportion by weight to glycol monoether 1.04 : 1). At a sump temperature of initially 70° C, which rose to 100° C, the glycol monoether was reacted to yield the corresponding formal by water separation with the aid of the entrainer.

The aqueous distillate contained 12.8 g (0.43 mole) of formaldehyde but no glycol monoether.

When the reaction was repeated with the same starting materials but without use of a column between the reaction flask and the water separator, the formaldehyde content in the aqueous distillate rose to 22.8 g (0.76 mole). In this case, too, no glycol monoether could be detected in the distillate.

EXAMPLE 4

In a flask 158 g (2 moles) of ethylene glycol monomethyl ether, 81 g of a 37% aqueous formaldehyde solution, 200 ml of $CH_2Cl_2$, corresponding to a proportion by weight to the glycol monoether of 1.72 : 1, were refluxed, while stirring, in the presence of 1.6 g of Amberlyst®15. A packed column having about 2 to 3 theoretical plates and a water separator were mounted between the 1 liter flask and the reflux condenser. The water of the formaldehyde solution and the water formed in the reaction were removed as an azeotrope. The temperature of the reaction mixture was in the range of from 50° to 60° C. After about 7 hours the reaction was terminated. The removed water had a formaldehyde content of 1.05 g (0.035 mole). The conversion of the glycol monoether was 93 mole % and the yield of glycol monoether formal amounted to 87.2 mole %, corresponding to a selectivity of 93.7 mole %, calculated on the glycol monoether.

To isolate the formal first methylene chloride and unreacted glycol monoether were separated over a column. The sump of the column consisted of almost pure formal which was subjected to distillation. The pure formal boiled at 102° to 104° C under 18 mm of mercury.

EXAMPLE 5

Under the conditions as specified in Example 4, the 37% formaldehyde solution (81 g) was added dropwise over a period of 3 hours to the ethylene glycol monomethyl ether together with the catalyst and $CH_2Cl_2$, while boiling and separating the water with the aid of the entrainer. In this case the formaldehyde content in the separated water was reduced to 0.4 g (0.01 mole %.) The yield of formal increased to 96.5 mole % with a selectivity of about 99 mole %, calculated on the glycol monoether used.

EXAMPLE 6

Under the conditions specified in Example 1, 600 g of diethylene glycol monomethyl ether, 30 g of Amberlyst® 15 and 1,000 ml of $CHCl_3$, corresponding to a proportion by weight to the diglycol monoether of 2.48 : 1, were heated to boiling temperature and, by means of a piston pump, 303 g of a 25% formaldehyde solution were uniformly pumped into the mixture over a period of 4 hours. The aqueous distillate contained 4.7 g of formaldehyde. The conversion of diglycol monoether was 91.7 mole %, the yield after distillation at a boiling point of 160° C under about 5 mm Hg amounted to 82 mole % of formal of the diglycol monoether.

EXAMPLE 7

Under the conditions specified in Example 4, water was removed as an azeotrope within a period of 3 hours from a mixture of 441 g of triethylene glycol monomethyl ether, 74 g of a 58% formaldehyde solution and 50 g of Amberlyst®15 by refluxing together with 600 ml of $CHCl_3$ (proportion by weight to triglycol monoether 2.03 : 1). The temperature in the reaction vessel was 70° to 80° C, the discharged water contained 3.8 g (0.13 mole) of formaldehyde. At a conversion of triglycol monoether of 75 mole % the formal was obtained, after distillation at 190°-220° C under 3 mm Hg, in a yield of 69.2 mole %, corresponding to a selectivity of 92.2 mole %.

EXAMPLE 8

750 g of a mixture of the following ethers were reacted with 37% formaldehyde solution in a manner analogous to to Example 1:

| | |
|---|---|
| triethylene glycol monomethyl ether | 9.0 % by weight |
| tetraethylene glycol monomethyl ether | 24.2 % by weight |
| pentaethylene glycol monomethyl ether | 28.8 % by weight |
| hexaethylene glycol monomethyl ether | 20.8 % by weight |
| heptaethylene glycol monomethyl ether | 10.8 % by weight |
| octaethylene glycol monomethyl ether | 4.7 % by weight |
| higher ethylene glycol monomethyl ether | 1.7 % by weight |

The mixture of the glycol monoethers was heated to boil at 70° - 80° C together with 1,500 g of $CHCl_3$ and 50 g of Amberlyst ®15 and during the course of 3 hours 121 g of a 37% formaldehyde solution were added dropwise whilst the water was removed with the aid of the entrainer. The aqueous distillate contained 3.9 g (0.13 mole) of formaldehyde. The catalyst was filtered off and the chloroform was distilled off under reduced pressure together with the residual amount of water and the unreacted formaldehyde. The catalyst, the activity of which was unchanged, could be used for further reactions. According to the decrease of the hydroxyl number from 6.9% to 1.9% the conversion to the formal of the glycol monoethers was 72.4%. Unreacted monoethers were distilled off at a sump temperature of up to about 280° C. Coloring matter in the residue was removed by adsorption with active carbon or bleaching earth.

EXAMPLE 9

In a 0.5 l three-necked flask provided with stirrer, thermometer and a packed column having about 2 to 3 theoretical plates on which a water separator was mounted for use of an entrainer having a density below 1.76 g (1 mole) of ethylene glycol monomethyl ether, 40 g of a 37% formaldehyde solution, 185 g of isopropyl chloride and 0.38 g of p-toluenesulfonic acid, corresponding to 0.5% by weight, calculated on the glycol monoether, were heated to boiling temperature while stirring. Over a period of 6 hours, 27 g of water were removed with the aid of the entrainer at rising temperature in the flask (38° to 56° C). The water contained 1.35 g of formaldehyde, corresponding to 9 mole % of the amount used, and traces of glycol monoether.

The yield of glycol monoether formal amounted to 72 mole % at a conversion of the glycol monoether of 78 mole %.

What is claimed is:

1. In a process for the production of an ethylene glycol monomethyl ether formal of the formula $[CH_3O(CH_2CH_2O)_n]_2CH_2$, wherein $n$ is from 1 to 8, by reacting the corresponding ethylene glycol monomethyl ether with a 20 to 60% by weight aqueous formaldehyde solution in the presence of from 0.2 to 20% by weight, calculated on the ether, of an acid having a pK value of less than 4, the improvement which comprises reacting said ether and aqueous formaldehyde solution in the presence of a halohydrocarbon selected from the group consisting of dichloromethane, trichloromethane, tetrachloromethane, ethylene dichloride, 1,1,2-trichloroethane, 1,1,2-trichloro-trifluoroethane, tetrachloroethylene, isopropyl chloride, propyl chloride, propylene dichloride and butyl chloride, and distilling off water in a mixture comprising an azeotrope of water with said halohydrocarbon.

2. The process defined in claim 1, wherein the reaction is carried out at a temperature of from 40° to 125° C.

3. The process defined in claim 1, wherein measured quantities of the aqueous formaldehyde solution are intermittently added to a boiling solution of the ethylene glycol monomethyl ether, the halohydrocarbon and the acid.

4. The process defined in claim 1, wherein the ratio by weight of the halohydrocarbon to the ethylene glycol monomethyl ether is from 0.2 : 1 to 5 : 1.

5. The process defined in claim 4, wherein the ratio is from 0.5 : 1 to 3 : 1.

6. The process as defined in claim 1, wherein said mixture is passed through a rectifying column containing about 2 or 3 theoretical plates.

7. The process defined in claim 1, wherein more than one ether of the formula $CH_3O(CH_2CH_2O)_nH$ is reacted.

8. The process defined in claim 1, wherein the ether and the formaldehyde of the aqueous formaldehyde solution are present in a ratio of 2 : 1.

9. The process defined in claim 1, wherein the halohydrocarbon is di-, tri-, or tetrachloromethane.

10. The process defined in claim 1, wherein the acid is a sulfonic acid group-containing ion exchanger.

* * * * *